США009144474B2

United States Patent
Faust et al.

(10) Patent No.: US 9,144,474 B2
(45) Date of Patent: Sep. 29, 2015

(54) TELESCOPIC ORTHODONTIC APPLIANCE

(71) Applicant: American Orthodontics Corporation, Sheboygan, WI (US)

(72) Inventors: Scott Eric Faust, Kiel, WI (US); Eric William Nimmer, Plymouth, WI (US); Lee John Vogel, Kiel, WI (US); Andrew M. Hayes, Chesterfield, MO (US)

(73) Assignee: American Orthodontics Corporation, Sheboygan, WI (US)

( * ) Notice: Subject to any disclaimer, the term of this patent is extended or adjusted under 35 U.S.C. 154(b) by 0 days.

(21) Appl. No.: 13/923,036

(22) Filed: Jun. 20, 2013

(65) Prior Publication Data
US 2014/0255866 A1     Sep. 11, 2014

Related U.S. Application Data (60) Provisional application No. 61/776,322, filed on Mar. 11, 2013, provisional application No. 61/776,309, filed on Mar. 11, 2013, provisional application No. 61/776,301, filed on Mar. 11, 2013.

(51) Int. Cl.
*A61C 7/36*    (2006.01)

(52) U.S. Cl.
CPC ........................................ *A61C 7/36* (2013.01)

(58) Field of Classification Search
CPC ........................................................ A61C 7/36
USPC ...................................................... 433/18–24
See application file for complete search history.

(56) References Cited

U.S. PATENT DOCUMENTS

| | | | |
|---|---|---|---|
| 3,798,773 A | 3/1974 | Northcutt | |
| 4,462,800 A * | 7/1984 | Jones | 433/19 |
| 4,618,324 A | 10/1986 | Nord | |
| 4,708,646 A | 11/1987 | Jasper | |
| 4,795,342 A * | 1/1989 | Jones | 433/19 |
| 5,562,445 A | 10/1996 | DeVincenzo et al. | |
| 5,678,990 A | 10/1997 | Rosenberg | |
| 5,738,514 A | 4/1998 | DeVincenzo et al. | |
| 5,829,975 A | 11/1998 | Gold | |
| 5,944,518 A | 8/1999 | Sabbagh | |
| 5,964,588 A * | 10/1999 | Cleary | 433/19 |

(Continued)

FOREIGN PATENT DOCUMENTS

| | | |
|---|---|---|
| DE | 29818960 | 1/1999 |
| EP | 1345547 B1 | 3/2011 |
| WO | 2013096090 | 6/2013 |

OTHER PUBLICATIONS

MiniScope Telescoping Herbst, www.americanortho.com, 17 pages, 2011.

(Continued)

*Primary Examiner* — Heidi M Eide
(74) *Attorney, Agent, or Firm* — Andrus Intellectual Property Law, LLP (57) ABSTRACT

An orthodontic appliance includes a telescopic assembly with an end tube and a telescopic member. A distal connector secured to the end tube at a generally distal end of the telescopic assembly. An end cap engages the distal end of the end tube. A spring is secured to the end cap and extends coaxially within the cover and the end tube. The spring is configured to impart a biasing force against the distal end of the telescopic member.

17 Claims, 9 Drawing Sheets

(56) References Cited

U.S. PATENT DOCUMENTS

| | | | |
|---|---|---|---|
| 6,053,730 | A | 4/2000 | Cleary |
| 6,234,792 | B1 | 5/2001 | DeVincenzo |
| 6,244,862 | B1 | 6/2001 | Hanks |
| 6,328,562 | B1 | 12/2001 | Sirney et al. |
| 6,358,046 | B1 | 3/2002 | Brehm et al. |
| 6,361,315 | B1 | 3/2002 | Hanks |
| 6,413,082 | B2 | 7/2002 | Binder |
| 6,558,160 | B2 | 5/2003 | Schnaitter et al. |
| 6,669,474 | B2 | 12/2003 | Vogt |
| 6,884,067 | B2 | 4/2005 | Tuneberg |
| 6,908,306 | B2 | 6/2005 | Bowman et al. |
| 6,964,566 | B2 | 11/2005 | Sapian |
| 6,976,839 | B2 | 12/2005 | Lluch |
| 6,988,888 | B2 | 1/2006 | Cleary |
| 7,070,410 | B2 | 7/2006 | Cacchiotti et al. |
| 7,238,022 | B2 | 7/2007 | Lluch |
| 7,578,671 | B2 | 8/2009 | Corcoran et al. |
| 7,578,672 | B2 | 8/2009 | Sheikh et al. |
| 7,618,257 | B2 | 11/2009 | Lluch |
| 2002/0025502 | A1 | 2/2002 | Williams |
| 2002/0132207 | A1* | 9/2002 | Tuneberg ............... 433/19 |
| 2004/0053188 | A1 | 3/2004 | Callabe et al. |
| 2004/0096798 | A1* | 5/2004 | Cleary ............... 433/18 |
| 2007/0190477 | A1 | 8/2007 | Sheikh et al. |
| 2010/0151402 | A1 | 6/2010 | Williams |
| 2011/0300503 | A1* | 12/2011 | Benvegnu et al. ............ 433/22 |
| 2012/0135365 | A1 | 5/2012 | Cleary |
| 2013/0177861 | A1* | 7/2013 | Hayes ............... 433/19 |

OTHER PUBLICATIONS

European Search Report in corresponding EP. 13003176, dated Sep. 9, 2014.

Dentaurum, SUS2, Sabbagh Universal Spring, a new dimension of Class II, improved version Brochure, 2014.

Hanandeh et al., "Evaluating the Effect of Sabbagh Universal Spring During Treatment of Growing Class II Malocclusions", IJO, vol. 21, No. 4, 2010.

Papadopoulos, Moschos, "Orthodontic Treatment of the Class II Noncomplaint Patient: Current Principles and Techniques", Elsevier Health Sciences, 2006, pp. 21-32.

Ritto, A. Korrodi, "Fixed Functional Appliances—A Classification (Updated)", The Orthodontic CYBERjournal, Jun. 2001. http://orthocj.com/2001/06/fixed-functional-appliances-a-classification-updated/.

* cited by examiner

TELESCOPIC ORTHODONTIC APPLIANCE

CROSS REFERENCE TO RELATED APPLICATION

This application relates to and claims priority from U.S. Provisional Application Ser. Nos. 61/776,301; 61/776,309; and 61/776,322 filed on Mar. 11, 2013, all of which are hereby incorporated by reference in its entirety.

FIELD OF THE DISCLOSURE

The present disclosure relates to the field of orthodontics. More specifically, the present disclosed relates to a telescoping orthodontic appliance employable for maxillary/mandibular bite correction.

BACKGROUND

Orthodontic treatment involves the movement of malpositioned teeth to desired positions. During typical treatment, orthodontic brackets are connected to anterior, cuspid, molar, and bicuspid teeth, and an archwire is placed in a slot of each bracket. The archwire guides movement of the brackets and the corresponding teeth to desired positions to correct occlusion. Traditionally, the ends of an archwire have been anchored by appliances known as buccal tubes that are secured to molar teeth (e.g., utilizing bands). More recently, archwire ends are increasingly being secured utilizing buccal tubes bonded directly to molar teeth (e.g., free from use of buccal tubes welded to bands).

Various types of spring devices and elastomeric devices may also be used in orthodontic treatment. The resilient forces of such devices in tension or compression may be used to secure an orthodontic appliance and an interconnected tooth or teeth and correspondingly facilitate movement relative to other orthodontic appliances and an interconnected tooth or teeth. For example, elastomeric rings may be employed as ligatures to secure an archwire in a slot of a bracket. As another example, elongated elastomeric devices (e.g., a chain of interconnected elastomeric ligatures) may be stretched between selected brackets in order to move certain teeth relative to other teeth. Yet other spring devices may be specifically designed to separate adjacent teeth or to rotate a tooth about its longitudinal axis.

The orthodontic treatment of some patients includes correction of the alignment of the maxillary dental arch and the mandibular dental arch. For example, certain patients have a condition referred to as a Class II malocclusion where the lower dental arch is located an excessive distance rearward of the upper dental arch when the jaws are closed. Other patients may have an opposite condition referred to as a Class III malocclusion wherein the lower dental arch is located forward of the upper dental arch when the jaws are closed.

Orthodontic treatment of Class II and Class III malocclusions typically entails movement of the maxillary dental arch (e.g., teeth comprising the maxillary arch) and/or movement of the mandibular dental arch (e.g., teeth comprising the mandibular arch). For such purposes, an activation force is often applied to teeth of each dental arch by applying a force to brackets, archwire or attachments connected to the brackets or archwires. These orthodontic appliances promote malocclusion treatment by restraining jaw movement which results in the biological response by the jaw and facial muscles that progressively corrects the malocclusion.

Additional forces can be added to the orthodontic appliance to apply a further corrective force that accelerate treatment and provide a biasing force as the patient reaches ends of the range of motion for the orthodontic appliance, adding to patient comfort. However, current solutions in orthodontic appliances suffer from problems with breakage and disengagement between the components of the orthodontic alliance, particularly if the patient opens their mouth beyond the functional range of the appliance or if appliance components are disengaged due to an external force. Solutions to these problems reduce patient comfort by extending the appliance beyond lengths needed to carry out treatment.

Orthodontic appliances generally extend between two or more teeth in the patient's dentition to apply the corrective forces. The orthodontic appliance can be secured on or about a tooth using a variety of techniques. Each of these techniques create significant drawbacks when an orthodontist desires to add an orthodontic appliance to the treatment of a patient once the patient has already been treated with braces (e.g., an archwire and bracket and/or buccal tubes). At a minimum, the addition of the orthodontic appliance requires complete or partial removal of the archwire such as to connect the orthodontic appliance to the archwire. In other cases, the existing bracket or buccal tube must be removed and replaced in order to add a specialized bracket or buccal tube or to add a molar band on the patient's tooth before replacing the buccal tube. All of this work takes orthodontist and patient time, increases treatment cost, and is discomforting to the patient. Furthermore, if an orthodontic appliance is to be removed, replaced, or repaired, often similar steps are required at the expense of time, money, and patient comfort.

BRIEF DISCLOSURE

An exemplary embodiment of an orthodontic appliance includes a telescopic assembly comprising at least an end tube with a hollow interior and first telescopic member telescopically disposed within the end tube. A distal connector is secured to the end tube at a generally distal end of the telescopic assembly. A mesial connector is secured to a generally mesial end of the telescopic assembly. A cover having a generally tubular shape is configured to removably engage and at least partially surround at least a portion of the end tube. The distal connector radially extends through a cutout in the cover. An end cap is secured to a distal end of the cover. The end cap removably engages a distal end of the end tube. A spring is secured at a distal end to the end cap and the spring extends away from the end cap coaxially within the cover and the end tube. The spring is configured to impart a biasing force against the end cap and a distal end of the telescopic member.

An exemplary embodiment of a method of treating a malocclusion with an orthodontic appliance includes securing an orthodontic appliance at mesial and distal ends to two locations within the dentition of the patient. The orthodontic appliance includes a telescopic assembly that includes at least an end tube with a hollow interior and a telescopic member telescopically disclosed within the end tube. The orthodontic appliance includes a distal connector secured to the end tube at a generally distal end of the telescopic assembly and a mesial connector secured to a generally mesial end of the telescopic assembly. The orthodontic appliance further includes a first interchangeable spring assembly that includes a cover with a generally tubular shape and configured to removably engage and at least partially surround at least a portion of the end tube such that the distal connector radially extends through a cutout in the cover. An end cap is secured to a distal end of the cover and a spring is secured at a distal end to the end cap and the spring extends away from the end cap coaxially within the cover and the end tube. The spring is configured to impart a biasing force against the end cap and the telescopic member. A second interchangeable spring assembly is selected from a plurality of interchangeable spring assemblies, each interchangeable spring assembly of the plurality is configured to impart an alternative biasing force against the distal end of the telescopic member. The first interchangeable spring assembly is removed from engagement with the end tube. The second interchangeable spring assembly engages the end tube. Treatment is progressed by imparting the alternative biasing force against the end cap and the telescopic member.

In a further exemplary embodiment of an orthodontic appliance, a telescopic assembly includes at least an end tube with a hollow interior and a telescopic member telescopically disposed within the end tube. A distal connector is secured to a generally distal end of the telescopic assembly. A mesial connector is secured to a generally mesial end of the telescopic assembly. An end cap engages the distal end of the end tube. A spring is secured at a distal end to the end cap and the spring extends away from the end cap coaxially within the end tube where the spring is configured to impart a biasing force against the end cap and the telescopic member.

DETAILED DISCLOSURE

Figure 1:
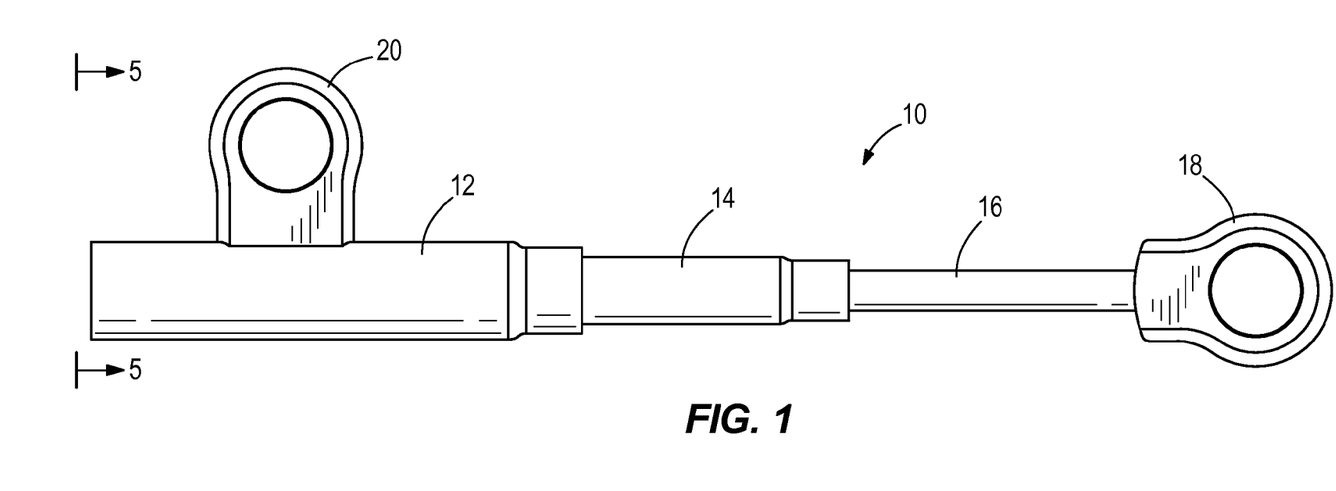
FIG. 1 depicts a side view of an exemplary embodiment of an orthodontic appliance.
Figure 2:
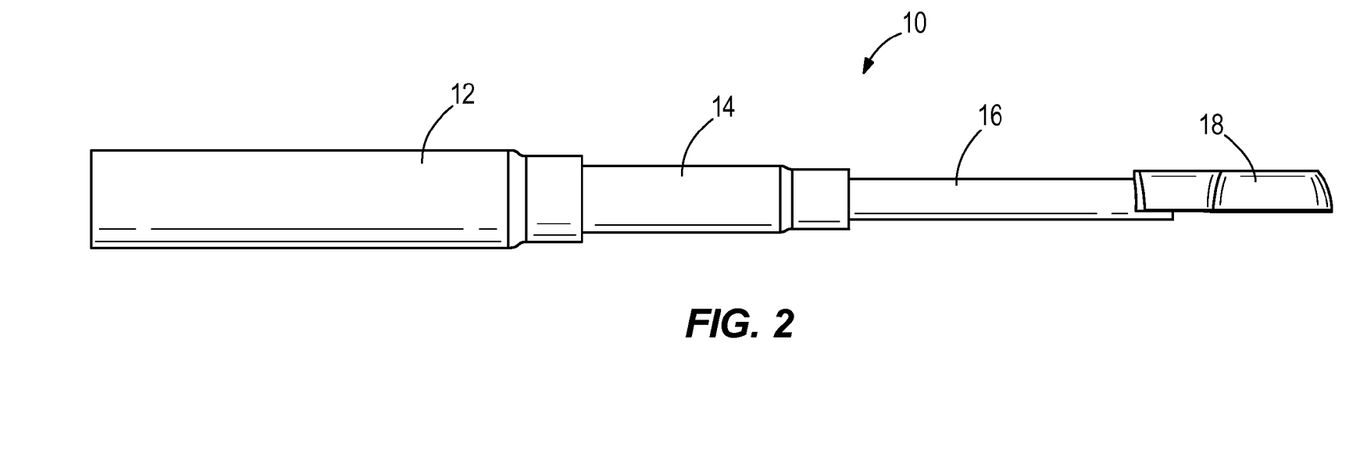
FIG. 2 is a bottom view of the exemplary embodiment of an orthodontic appliance of FIG. 1.

FIGS. 1 and 2 depict an embodiment of an orthodontic appliance 10 which is exemplarily a class II corrector configured to treat over bite malocclusions. It will be understood that while a class II corrector is used exemplarily herein, embodiments as disclosed herein may apply to other orthodontic appliances. The orthodontic appliance 10 is designed in a telescoping manner from a distal end to a mesial end with an end tube 12, a middle tube 14, and a rod 16. The telescoping configuration of these components can be seen in greater detail in FIG. 5, which is a cutaway view of the orthodontic appliance 10 of FIG. 1 taken along line 5-5. It is to be noted that in embodiments respective mesial/distal ends of adjacent telescoping components are configured such that the components are retained in a telescoping manner, exemplarily such that the end tube 12, middle tube 14 and rod 16 are not separable from the orthodontic appliance 10.

Referring back to FIG. 1, the orthodontic appliance 10 includes a mesial connector 18 and a distal connector 20. In a non-limiting embodiment, the mesial connector 18 and the distal connector 20 are eyelets configured to receive a screw therethrough that secures the connector to the braces on the patient. In a non-limiting embodiment, the mesial connector 18 is configured to secure to or about the cuspid on the lower jaw, while the distal connector 20 is configured to be secured on or about the first molar of the upper jaw; however, it will be recognized that in alternative embodiments, the exact positioning of the appliance within the mouth of the patient may be made between other positions. The mesial connector 18 and the distal connector 20 may be secured on or about the respective teeth of the patient in a variety of ways, including, but not limited to, connection to direct bonded or band bonded buccal tubes, direct connections to molar bands, or connections to archwires at a location near the tooth.

Figure 5:
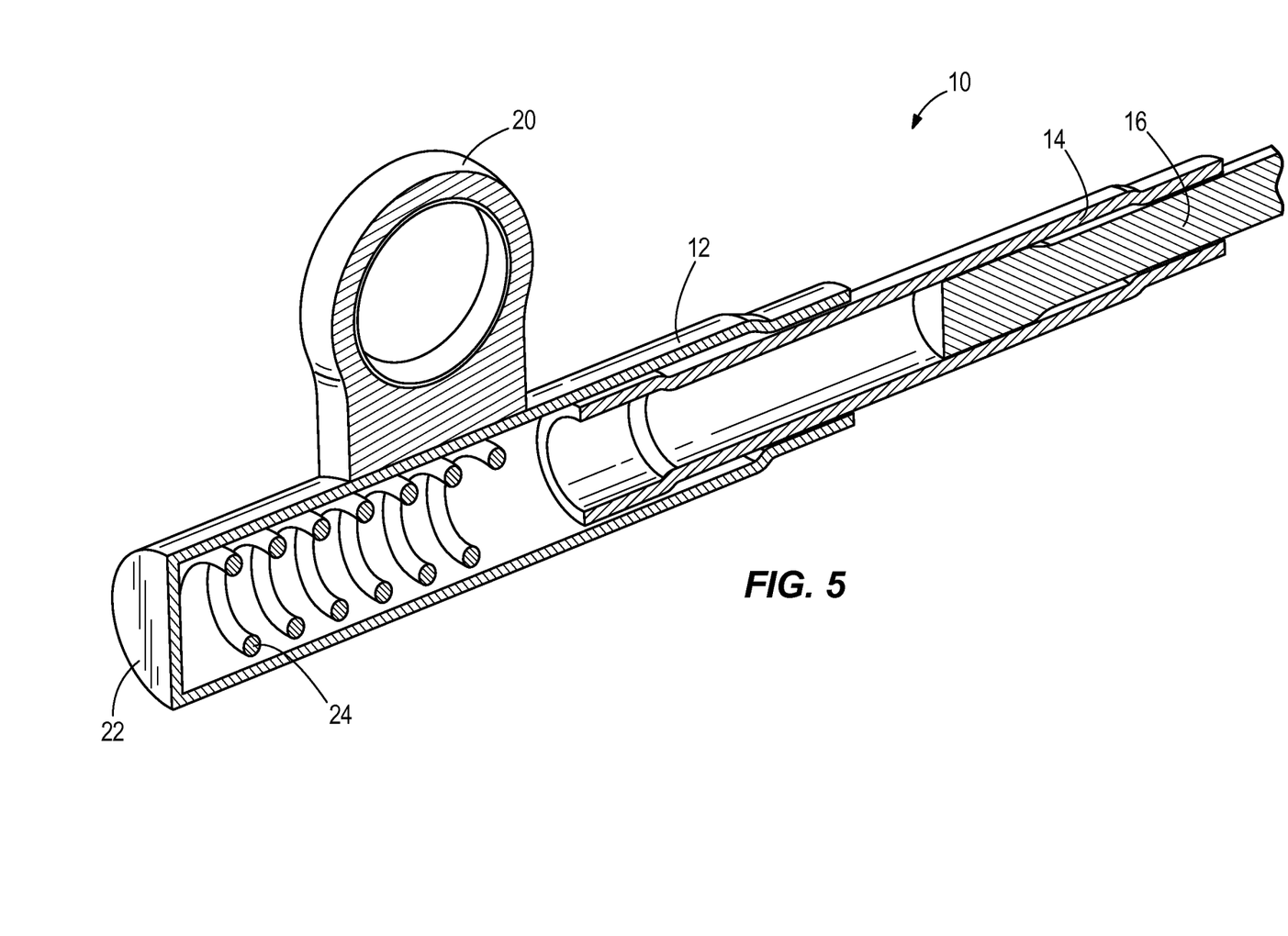
FIG. 5 depicts a partial cutaway view taken along line 5-5 of FIG. 1.

The embodiment of the orthodontic appliance 10 depicted in FIGS. 1, 2, and 5 includes an exemplary location of the distal connector 20 and represents a generally mesial orientation for the distal connector 20. In the mesial orientation of the distal connector 20, the end tube 12 extends distally beyond the distal connector 20 and terminates in an end cap 22. The end cap 22 closes the distal end of the end tube 12 and secures a spring 24 within the end tube 12. The spring is configured to be of a dimension that fits within the inside diameter of the end tube 12 yet is constructed in order to produce the desired treatment force. The spring 24 specifically applies a force between the end cap 22 and a distal end 26 of the middle tube 14. This specifically applies the additional treatment force on the patient's lower jaw as the patient's lower jaw reaches a closed position. Previous solutions had placed incremental mechanical stops, exemplarily on the rod 16, in order to progressively limit lower jaw movement. However, the inventors have discovered that this adds to patient discomfort as the mechanical stops provide an abrupt end to lower jaw movement whereas the spring 24 begins to progressively apply a resilient force against lower jaw movement as the patient's lower jaw closes.

In exemplary embodiments, the spring 24 may apply 400 grams of force, while in other embodiments, the spring may apply 200 grams of force or 240 grams of force; however, other spring forces are considered to be within the scope of the present disclosure. In further exemplary embodiments, different spring lengths may carry out different treatment effects, such as controlling the effective spring engagement range when the additional spring force is applied as the patient closes the patient's jaw.

Figure 3:
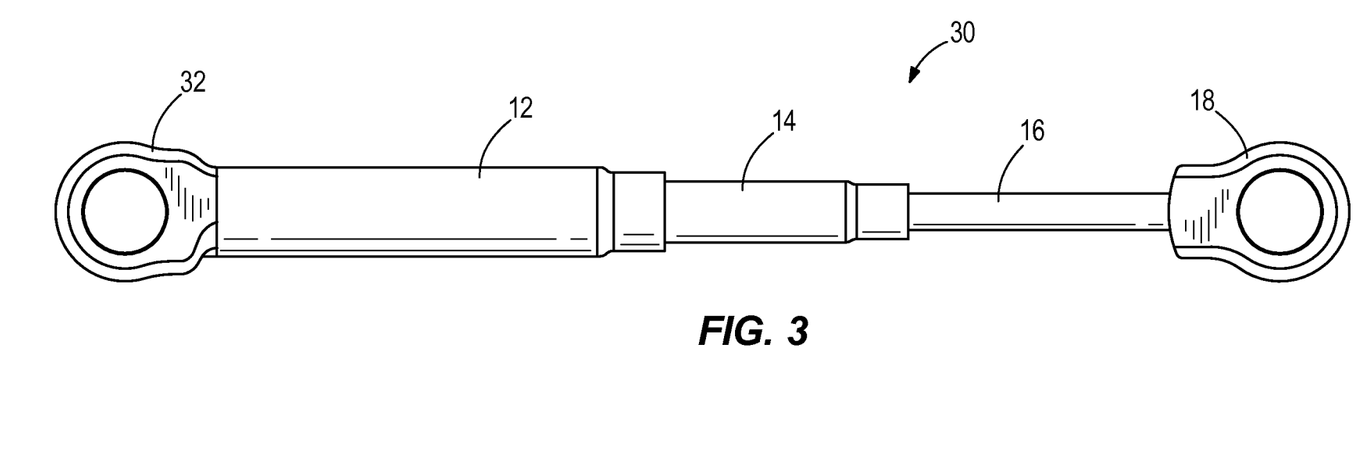
FIG. 3 depicts a side view of an exemplary alternative embodiment of an orthodontic appliance.
Figure 4:
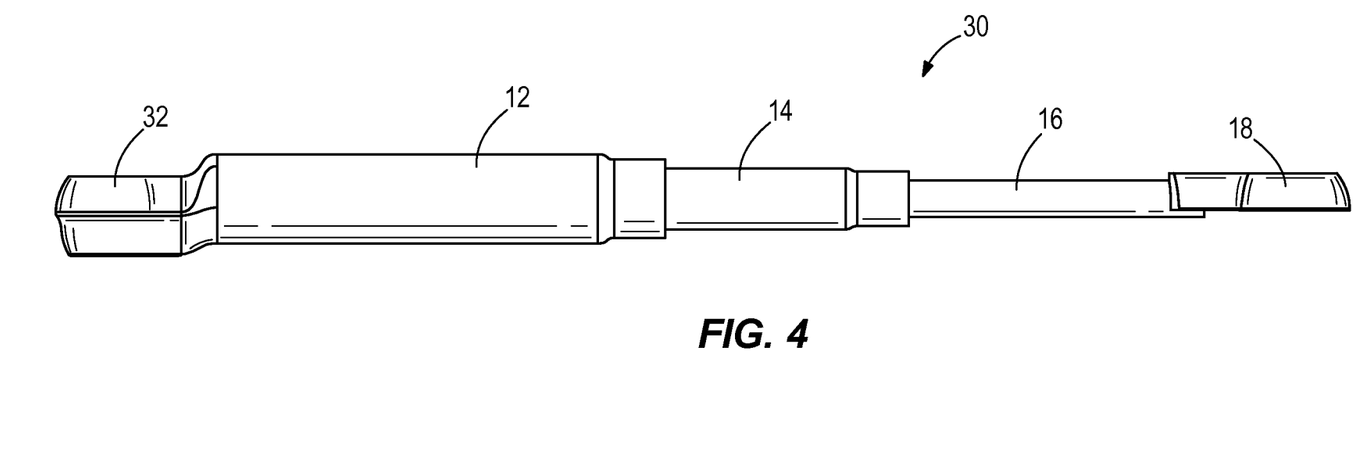
FIG. 4 depicts a bottom view of the exemplary alternative embodiment of an orthodontic appliance of FIG. 3.

FIGS. 3 and 4 depict an alternative embodiment of an orthodontic appliance 30. It should be noted in FIGS. 3 and 4 like reference numerals have been used to identify like features from the description above with respect to FIGS. 1, 2 and 5 for the purposes of conciseness. The orthodontic appliance 30 differs from the orthodontic appliance 10 in that the distal connector 32 of the orthodontic appliance 30 is located at the far distal end of the end tube 12. In the orthodontic appliance 30, the distal connector 32 also serves the function previously performed by the end cap 22 in the orthodontic appliance 30 in that the distal connector 32 seals a distal end of the end tube 12.

The inventors have found that the embodiment of the orthodontic appliance 30 provides still further advantages to the field of orthodontic appliances. The orthodontic appliance 30 provides the further advantage of aligning the attachment points of the orthodontic appliance with the spring force applied by the spring (not depicted) internal to the end tube 12. This alignment of the orthodontic appliance connection points with the additional treatment force provided by this spring aids treatment by eliminating or reducing a lever force created by the offset between the treatment force and the connection points in previous designs. Additionally, with the distal connector 32 at the distal end of the orthodontic appliance 10, the orthodontic appliance 30 does not extend distally of the connection point to promote patient comfort by making the orthodontic appliance 30 more compact within the mouth of the patient.

It is to be understood that the exemplary embodiments of the orthodontic appliance shown in FIGS. 1-5 are merely exemplary of placements of the distal connector. In other embodiments, the distal connector may be located at any position between the two distal connector positions as exemplarily shown between FIGS. 1 and 3. In a further non-limiting embodiment (not depicted), the distal connector may extend at exemplarily a 45° angle from the end tube such as to balance between the embodiments depicted.

It is further to be noted that, while not depicted, in embodiments wherein the distal connector is not located at the distal end of the orthodontic appliance, the end tube of the orthodontic appliance may be open at the distal end of the end tube. In such embodiment, the distal end of the end tube may include a crimp or lip (not depicted) that retains the spring within the end tube of the orthodontic appliance.

Embodiments of the presently disclosed orthodontic appliance present still further embodiments over currently available solutions. Specifically, by enclosing the end tube 12 and enclosing the spring 24 within the end tube 12, these known traps for food and/or bacteria are eliminated, resulting in an orthodontic appliance that is easier for a patient to clean and may reduce bacteria growth in the patient's mouth about the orthodontic appliance. By enclosing the spring within the telescoping orthodontic appliance, the spring, which is known to be difficult to clean and a harbor for food and/or bacteria is limited from access to food and/or bacteria, while closing the distal end of the end tube further limits food and bacteria access to the interior of the end tube and/or middle tube, limiting these locations as regions for bacteria growth.

Figure 6:
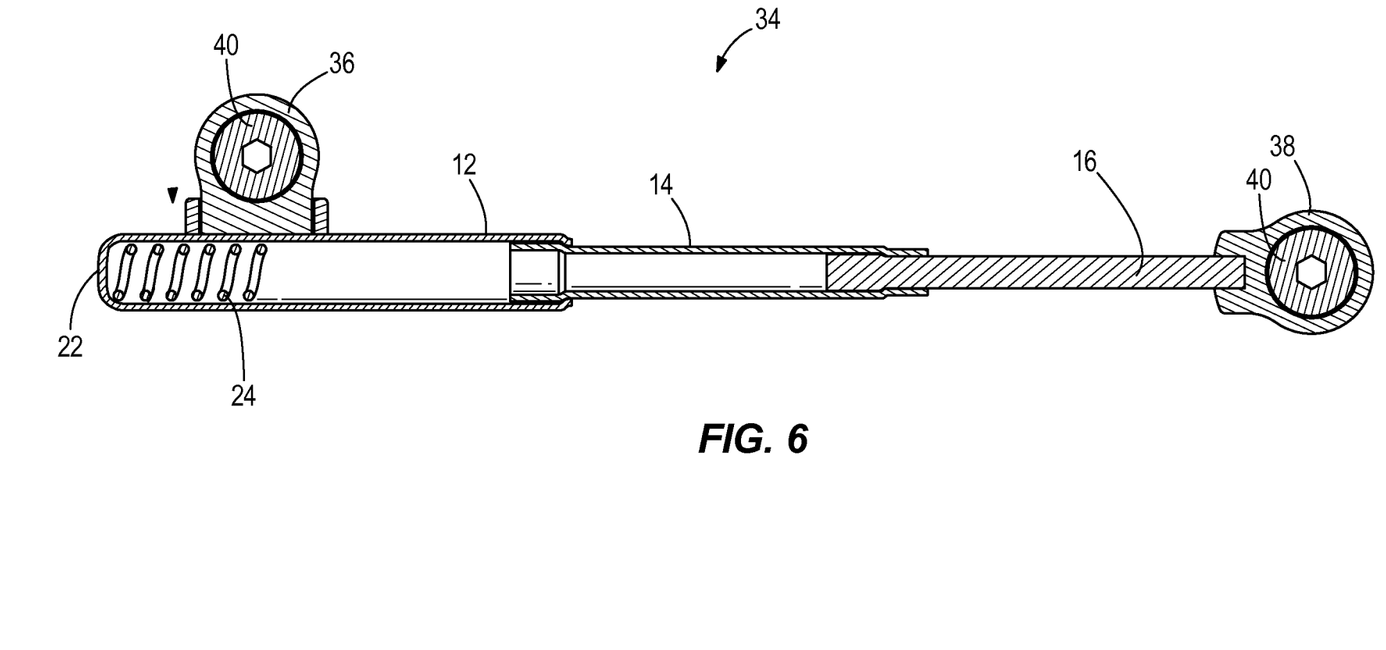
FIG. 6 is a cut away view of an alternative embodiment of the orthodontic appliance of FIG. 1 that includes integral connection screws.

FIG. 6 depicts an exemplary alternative embodiment of an orthodontic appliance 34 in which the distal connector 36 and the mesial connector 38 further include an integral connection screw 40. The integral connection screws 40 may be in the form of a cup-and-ball configuration with the distal connector 36 and the mesial connector 38. In some embodiments, such a cup-and-ball arrangement promotes patient comfort by providing an extra degree of movement between the orthodontic appliance and the patient's dentition while not compromising the corrective treatment provided by the orthodontic appliance 34. Such an integral configuration further reduces orthodontists' time in assembling the orthodontic appliance while eliminating the risk that an orthodontist drops a screw into the patient's mouth during installation or removal of the orthodontic appliance. In some embodiments, the connection screws 40 include hexalobular fasteners which shape gives increased resilience of the screw head to stripping from the driver or fastener head.

Embodiments of the connection screws 40 are configured to secure to a variety of threaded mounts to secure the orthodontic appliance relative to the patient's dentition. These threaded mounts may include threaded connections integrated with a buccal tube or bracket mounted to a tooth, a band secured around a tooth, or may be integrated with a connector secured to an archwire. Exemplary embodiments of archwire connectors are disclosed herein.

In exemplary uses of embodiments of the orthodontic appliances depicted in FIGS. 1-6, an orthodontist may progress treatment by interchangeably replacing the orthodontic appliance with another orthodontic appliance of a plurality of available orthodontic appliances. Each alternative orthodontic appliance may vary in the spring disposed within the end tube such that differing forces or effective engagement ranges are achieved by different orthodontic appliances. The combinational use of the orthodontic appliance with archwire connectors as disclosed in greater detail herein may further facilitate this interchangeability.

Figure 7:
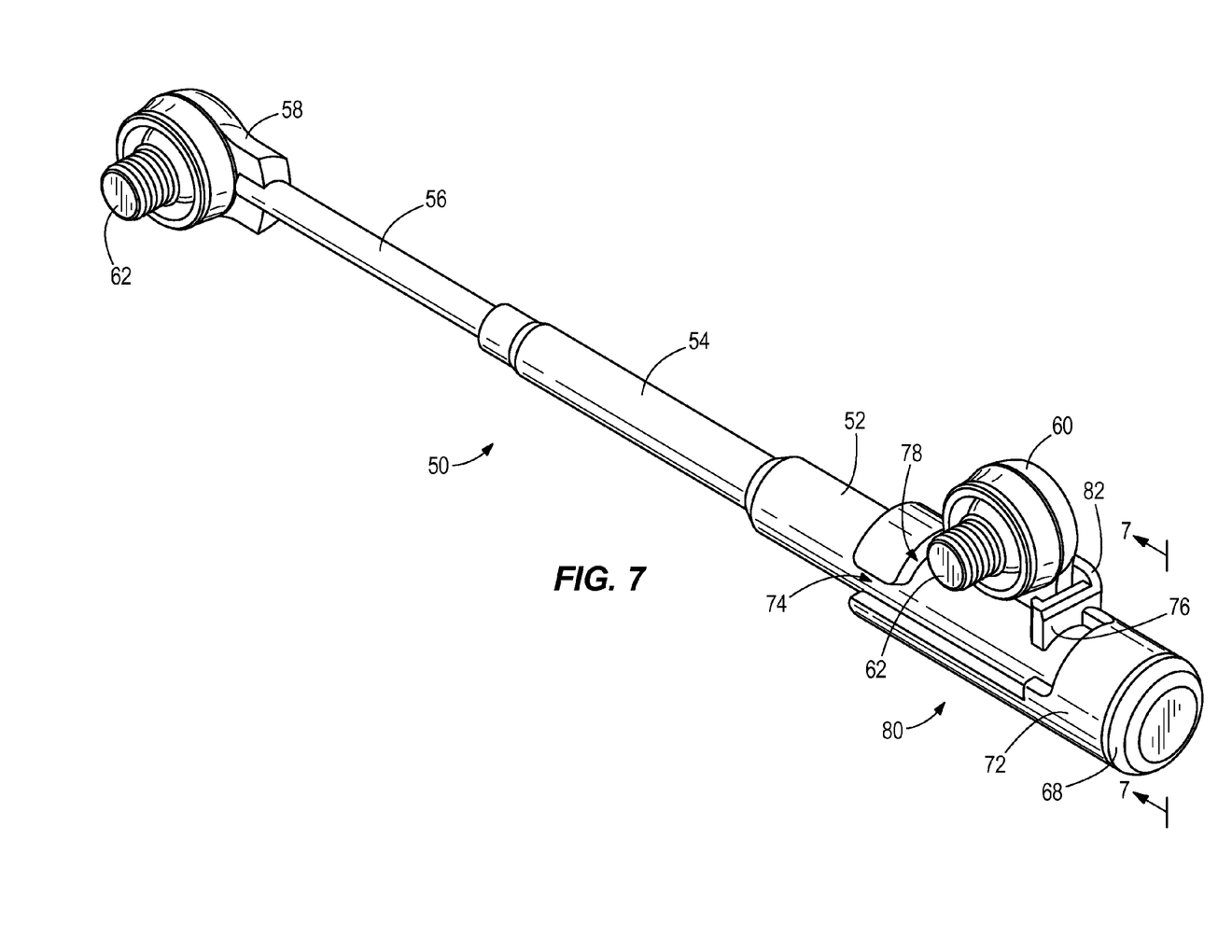
FIG. 7 is an isometric view of an exemplary alternative embodiment of a telescopic orthodontic appliance.

FIG. 7 depicts an exemplary alternative embodiment of an orthodontic appliance 50 which is exemplarily a Class II corrector configured to treat over bite malocclusions. The orthodontic appliance 50 is designed in a telescoping manner from a distal end to a mesial end with a plurality of telescoping members, exemplarily an end tube 52, a middle tube 54, and a rod 56. The telescoping configuration of these components can be seen in greater detail in FIG. 8, which is a cutaway view of the orthodontic appliance 50 of FIG. 7 taken along line 7-7.

Referring back to FIG. 7, the orthodontic appliance 50 includes a mesial connector 58 and a distal connector 60. In the non-limiting embodiment depicted, the mesial connector 58 and distal connector 60 have integrated screws 62 in a cup-and-ball configuration to join the screw 62 to the orthodontic appliance as described above with respect to FIG. 6

The mesial connector 58 and the distal connector 60 operate to secure the orthodontic appliance 50 to the braces on the patient. In a non-limiting embodiment, the mesial connector 58 is configured to secure to or about the cuspid on the lower jaw, while the distal connector 60 is configured to be secured on or about the first molar of the upper jaw; however, it will be recognized that in alternative embodiments, the exact positioning of the appliance within the mouth of the patient may be made between other positions. The mesial connector 58 and the distal connector 60 may be secured on or about the respective teeth of the patient in a variety of ways, including, but not limited to, connection to direct bonded or hand bonded buccal tubes, direct connections to molar bands, or connections to archwires at a location near the tooth.

Figure 8:
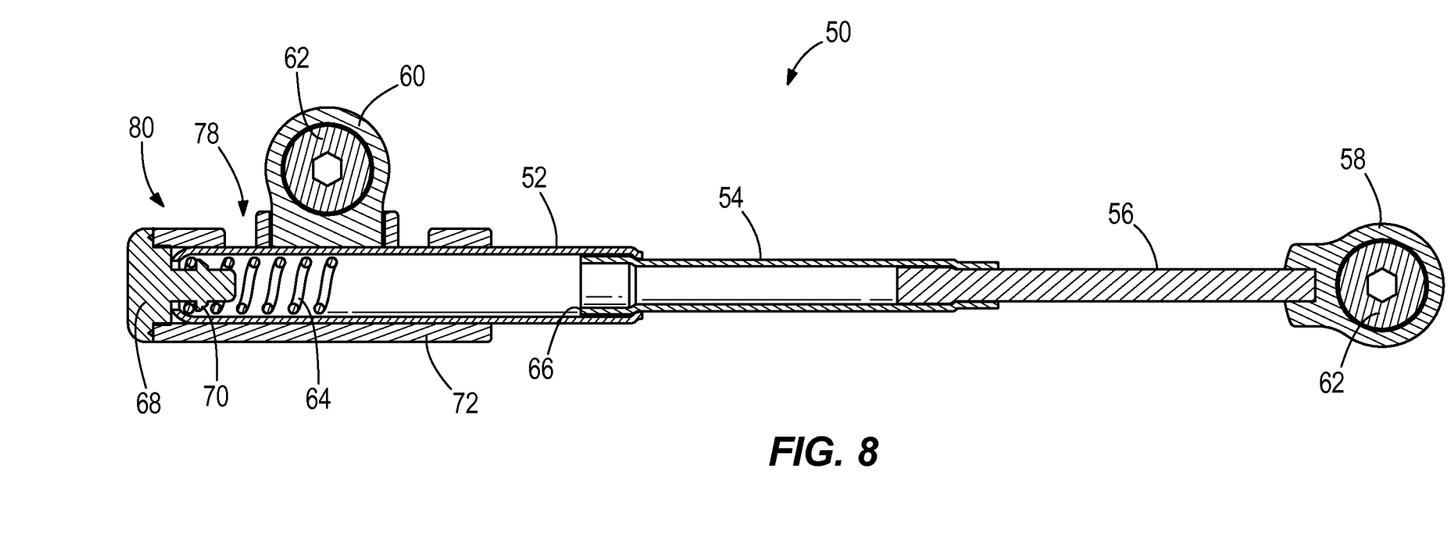
FIG. 8 is a cutaway view of the exemplary alternative embodiment of a telescoping orthodontic appliance of FIG. 7 taken along line 7-7.

FIG. 8 is a cutaway view of the orthodontic appliance of FIG. 7 taken along line 7-7. The cutaway view of FIG. 8 shows the telescoping nature of the end tube 52, middle tube 54, and rod 56 of the orthodontic appliance 50 in better detail. A spring 64 is disposed interior to the end tube 52. The spring 64 is configured to be of a dimension that fits within the inside diameter of the end tube 52, yet is constructed, in order to produce the desired treatment force as described in further detail herein. The spring 64 specifically applies a force against a distal end 66 of the middle tube 54 which applies an additional treatment force on the patient's lower jaw as the patient's lower jaw reaches a closed position. Previous solutions have placed incremental mechanical stops (not depicted), exemplarily on the rod. 56, in order to progressively limit lower jaw movement as the patient's treatment progressed. However, this adds to patient discomfort as mechanical stops provide an abrupt end to lower jaw movement whereas the spring 64 begins to progressively apply a resilient force against lower jaw movement as the patient's lower jaw closes.

The spring 64 is secured at a distal end to an end cap 68 that secures about an open distal end of the end tube 52. The end cap 68 exemplarily includes a lip 70 that is configured to retain the spring 64 in connection with the end cap 68. The end cap 68 is connected to a cover 72 that extends about at least a portion of the end tube 52. In an embodiment, the cover 72 is shaped in a generally tubular configuration to fit the end tube 52. Thus, in embodiments, the spring 64, end cap 68, and cover 72 are secured to one another as an interchangeable spring assembly 80, such that these components can be moved together. Specifically, in embodiments, the combined cover 72, end cap 68, and spring 64 are removable from connection with the end tube 52.

In embodiments, a plurality of separate configurations of interchangeable spring assemblies 80 which each comprise springs, end caps, and covers as described herein are available for use by an orthodontist. Each assembly may include a spring of a varying spring length and/or force such as to impart differing treatment effects these effects could differ in range of effective spring, engagement, a degree of corrective force, or a combination thereof. As described in further detail herein, an orthodontist may choose to use a combination of spring lengths over the course of orthodontic treatment with different spring lengths and/or forces being used at different stages of the treatment. Alternatively, an orthodontist may select from the varying lengths of springs and/or forces in order to customize the orthodontic treatment to the corrective action required by a specific patient.

In embodiments, the cover 72 is configured such as to facilitate removal and replacement of the interchangeable spring assembly 80 from connection with the end tube 52. Such configuration of the cover 72 may include a key slot 74 that is configured to enable a portion of the cover 72 to slide past the distal connector 60, and as latch 76 or other retaining device that secures the cover 72 in relation to the distal connector 60. In a non-limiting example depicted in FIGS. 7 and 8, the cover 72 further includes a cut out 78 through which the distal connector 60 extends. The distal connector 60 is received within the cut out 78. The latch 76 retains the distal connector 60 in the cut out 78. In use, the interchangeable spring assembly 80 is coaxially connected with the end tube 52 and is translated with respect to the end tube 52 such that the distal connector 60 passes through the key slot 74 in the cover 72. Once the distal connector 60 is distal of the key slot 74, the cover 72 is rotated about the end tube 52 such that the latch 76 engages the distal connector 60, retaining the distal connector 60 within the cut out 78. This process inserts the spring 64 into the open interior of the end tube 52 and arranges the spring 64 in the proper alignment for operation with the middle tube 54. This process further engages the open distal end of the end tube 52 with the end cap 68, closing off the open distal end of the end tube 52.

The process is generally reversed in order to remove the interchangeable spring assembly 80 as described in further detail herein. In order to facilitate removal, the cover 72 can include a projection 82 that is configured to be engaged by a finger or tool of an orthodontist in order to disengage the latch 76 from the distal connector 60.

In an embodiment, the end cap 68 may be configured with identifying information, including, but not limited to, an indication of the spring length to which the end cap 68 is connected and/or a configuration of orthodontic appliance for which the interchangeable spring assembly 80 is configured. As a non-limiting example, the end cap 68 may include an indication that such assembly is configured for use on the right hand side of a patient's mouth as opposed to configured for use on a left hand side of a patient's mouth. In one non-limiting embodiment, the end cap may convey such information through the use of alpha numeric indicators or by color coding, or some other indication system.

In exemplary embodiments, spring 64 may apply 400 grams of force, while in other non-limiting embodiments, the spring may apply 200 grams of force, or 240 grams of force; however, other spring forces are to be considered within the scope of the present disclosure. In embodiments, the spring force may be consistent across a variety of offered spring lengths, and therefore in some embodiments the differences between the corrective therapy applied by each of the variety of available springs is based upon differences in available spring lengths, and the resulting difference in effective spring engagement range. In still further embodiments, both spring force and spring length may be varied.

Embodiments of the orthodontic appliances disclosed herein present the advantage of providing a telescopic orthodontic appliance with interchangeable activation springs that due to the configuration of the interchangeable spring assembly 80 can be easily changed either for purposes of replacement or to change the length of the spring used with the orthodontic appliance without replacing the orthodontic appliance itself or, in embodiments, without disconnecting the orthodontic appliance 50 from connection to the braces in the mouth of the patient. The features of the cover 72 as disclosed herein enable the interchangeable spring assembly 80 to engage and disengage from the orthodontic appliance while the orthodontic appliance remains in place.

As best depicted in FIGS. 6-8, embodiments of orthodontic appliances disclosed herein may have distal connectors and mesial connectors that include screws which are integral to the orthodontic appliance such as using a cup-and-ball configuration described above in order to join the screws to the orthodontic appliance. This promotes patient comfort by providing an extra degree of movement between the orthodontic appliance, and the patient's dentition while not compromising the corrective treatment provided by the orthodontic appliance. This extra degree of movement can further facilitate the exchange of interchangeable spring assemblies while maintaining the attachment of the mesial and distal connectors to the patient's braces or dentition. Such an integral configuration further reduces orthodontist time in assembling the orthodontic appliance while eliminating the risk that the orthodontist drops a screw into the patient's mouth during, installation or removal of the orthodontic appliance. It is also to be recognized that in embodiments, the screws have hexalobular fasteners which shape gives increased resilience of the screw head to stripping from the driver or fastener head.

Figure 9:
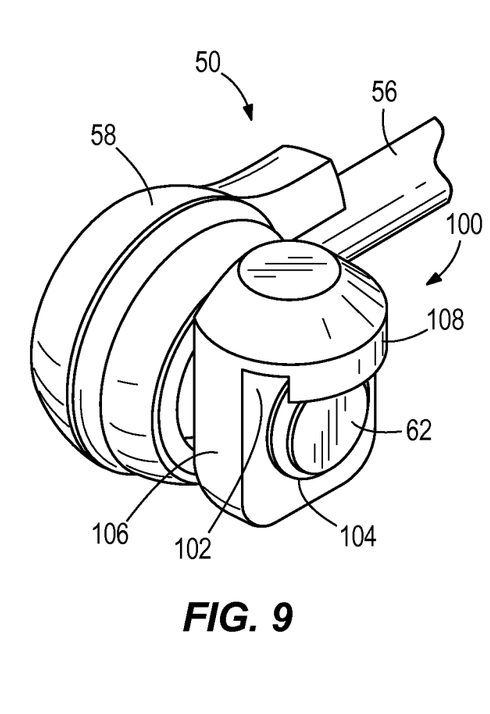
FIG. 9 is an isometric view of a first exemplary embodiment of an archwire connector.

FIG. 9 depicts an exemplary embodiment of an archwire connector 100. The archwire connector 100 is configured to facilitate the connection of the orthodontic appliance to an archwire of the patient's braces. FIG. 9 exemplarily depicts the mesial connector 58 of the orthodontic appliance shown in FIGS. 6-8; however, it will be recognized that this is for exemplary purposes and alternative archwire connector embodiments similar to those as depicted and described herein may similarly be used in conjunction with any of the embodiments of distal connectors, mesial connectors, and other alternative embodiments of orthodontic appliances within the scope of the present disclosure, including any of those embodiments depicted in FIGS. 1-8.

Figure 10:
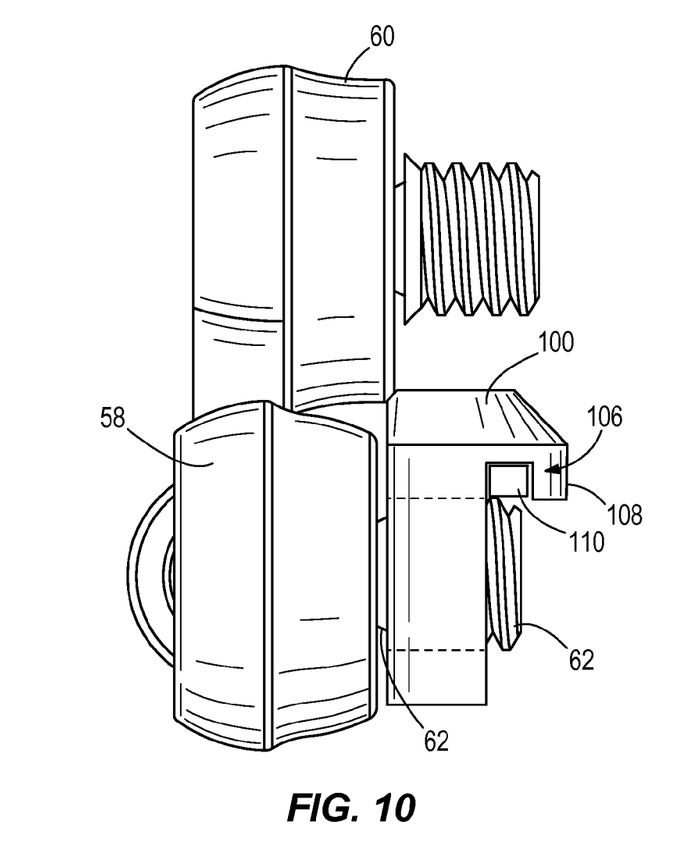
FIG. 10 is a side view of the first exemplary embodiment of the archwire connector of FIG. 9.

FIG. 10 is a side view of the embodiment depicted in FIG. 9. The archwire connector 100 includes a connector body 102 that has a threaded through-hole 104 configured to receive the screw 62 of the mesial connector 58. The archwire connector 100 further includes a wire slot 106 defined at least in part by a lip 108. As depicted in FIG. 10, the wire slot 106 and lip 108 are configured such as to at least partially surround an archwire 110 (shown in cross section in FIG. 10) at a location defined by the wire cut-out 106 and the screw 62. In an embodiment, the screw 62, when extending through the through-hole 104 obstructs the wire cut-out 106 in a way such as to movably restrain the archwire 110 within the archwire slot 106. It will be recognized that in one embodiment, the screw 62 may fixedly secure the archwire connector 100 to the archwire 110, or in a still further exemplary embodiment, the screw 62 may have multiple positions within the through-hole 104 such that in a first position the archwire connector 100 is free to be moved into and out of engagement with the archwire 110, while in a second position, the archwire connector 100 is free to translate along the archwire 110 with the archwire 110 retained in the wire slot 106, while in a third position of the screw 62, the archwire connector 100 is fixedly secured to the archwire.

In use, the orthodontist may hang the archwire connectors 100 on the patient's installed archwire 110, without removing or partially removing the archwire 100 from engagement with any of the buccal tubes or brackets (not depicted) in the patient's braces and then the orthodontist can engage the through-hole 104 of the archwire connectors 100 with the screws 62 of the orthodontic appliance. In an alternative embodiment, the orthodontist may secure the archwire connectors 100 to the screws 62, such as in the above described exemplary first position, and then engage the patient's archwire 100 with the wire slots 106 of the archwire connector 100 before tightening the screws 62 in order to retain the archwire within the wire slot 106. In either embodiment, the orthodontist need not disengage the archwire from any of the buccal tubes or brackets already secured to the patient's teeth and therefore the archwire connector 100 facilitates placement of the orthodontic appliance. Removal of the orthodontic appliance either due to the end of treatment, or to replace or repair the orthodontic appliance is similarly facilitated as the orthodontist need only to reverse the steps to remove the archwire connector 100 from engagement with the patient's archwire.

Figure 11:
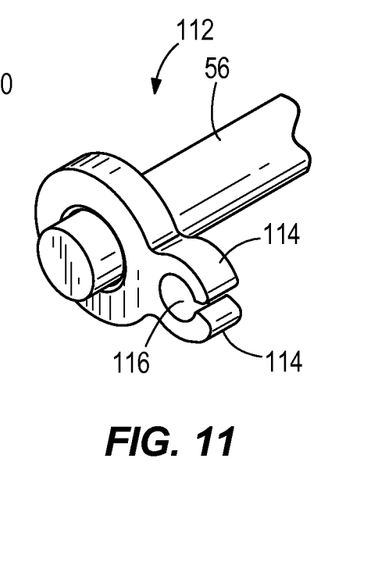
FIG. 11 is an isometric view of an exemplary alternative embodiment of an archwire connector.

FIG. 11 depicts an alternative embodiment of an archwire connector 112. The archwire connector 112 further replaces the mesial connector depicted in FIG. 9 and is directly connected to the rod 56 of the orthodontic appliance. It is to be understood that in embodiments, the archwire connector 112 may be fixedly or movably secured to the rod 56. The archwire connector 112 includes opposed resilient arms 114 that are made of a resilient material, such that the resilient arms 114 are flexible enough such as to deform around an archwire such as to place an archwire (not depicted) within an archwire bore 116 of the archwire connector 112. It is to be recognized that embodiments, the archwire bore 116 may be dimensioned in a manner such as to either fixedly or movably engage the archwire. In a non-limiting embodiment, if the archwire bore 116 is dimensioned such as to movably engage the archwire, in one such embodiment, the archwire connector 112 translates along the archwire, exemplarily between two orthodontic brackets bonded to teeth of the patient.

In a non-limiting embodiment, the resilient arms 114 may be constructed of a nickel titanium alloy or other such alloy or material that is both easily manipulated by the orthodontist to engage the archwire, while retaining its shape in a sufficient capacity such as to sufficiently secure the end of the orthodontic appliance to the archwire.

Figure 12:
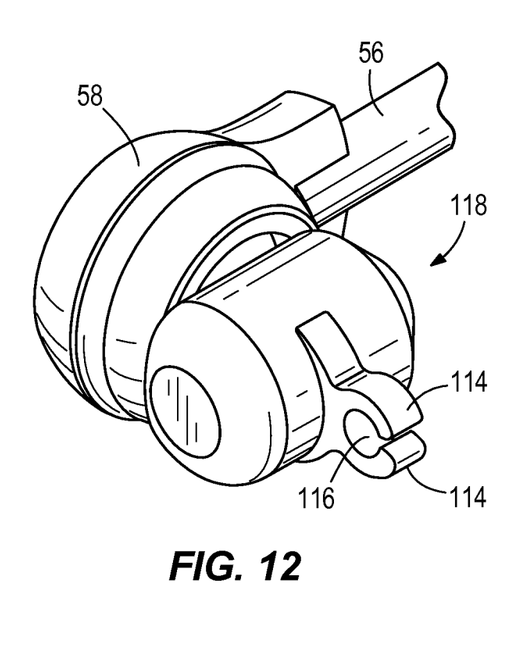
FIG. 12 is an isometric view of a third exemplary embodiment of an archwire connector.
Figure 13:
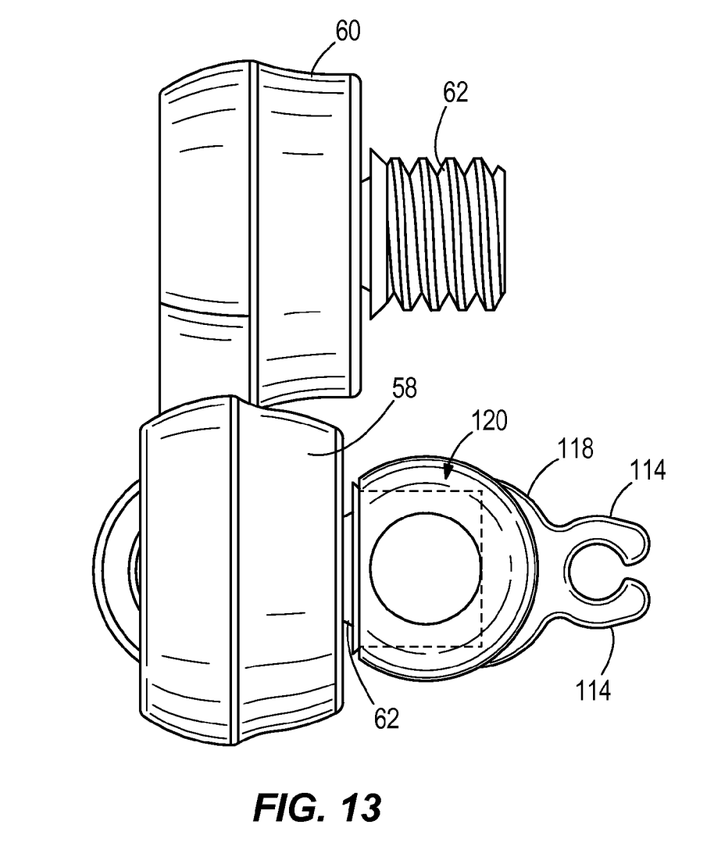
FIG. 13 is a side view of the third exemplary embodiment of FIG. 12.

FIGS. 12 and 13 depict a still further exemplary embodiment of an archwire connector 118. The archwire connector 118 combines elements of the embodiments depicted in FIGS. 9-11 in that the archwire connector 118 includes a pair of resilient arms 114 that are configured as described above with respect to FIG. 11 to resiliently deform to accept the archwire within an archwire bore 116. The archwire connector 118 is secured to the orthodontic appliance by way of a threaded connection 120 configured to receive the screw 62 of the mesial connector 58. Thus, the archwire connector 118 may be used in a similar manner as described above with respect to the archwire connector 100 in that the archwire connector 118 may either be first removably secured to the archwire (not depicted) and then the threaded bore 120 engaged with the screw 62 of the mesial connector 58 or that the archwire connector 118 may be threadedly secured to the mesial connector 58 prior to orthodontist installation of the orthodontic appliance, and then the resilient arms 114 of the archwire connector 118 used to removably secure the mesial connector 58 to the archwire.

Figure 14:
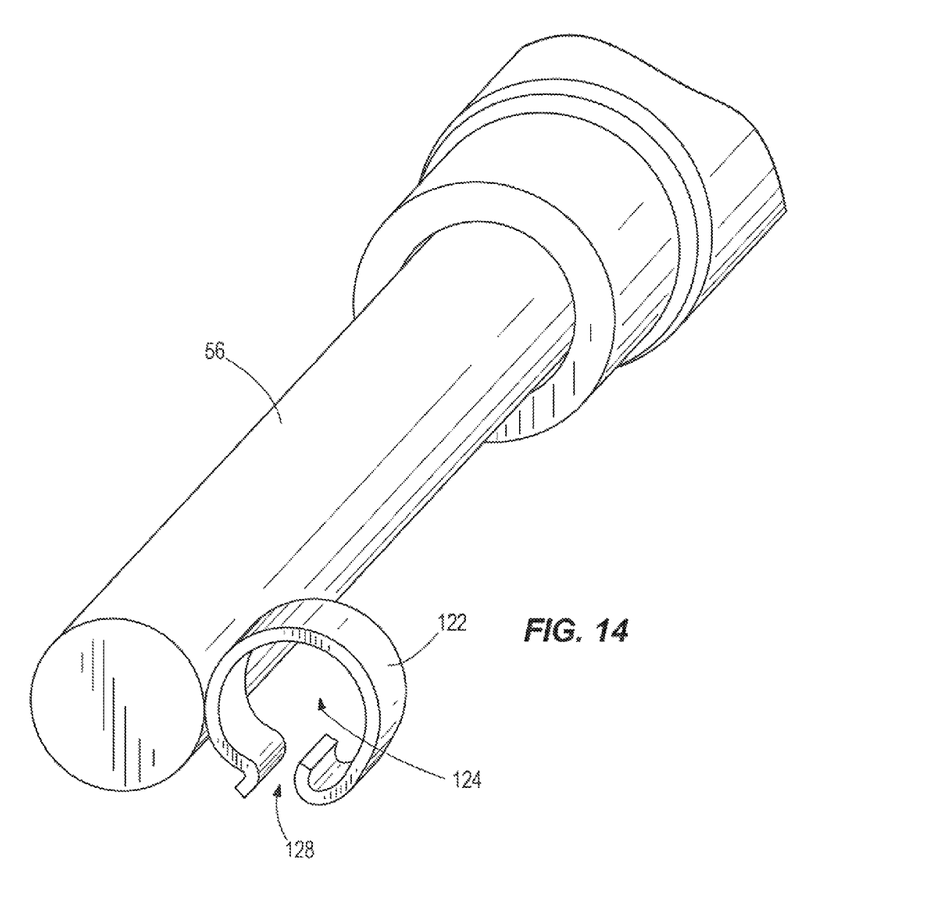
FIG. 14 is an isometric view of a fourth exemplary alternative embodiment of an archwire connector.

FIG. 14 depicts an exemplary embodiment of a still further alternative embodiment of an archwire connector 122 similar to the archwire connector 112 depicted in FIG. 11, in that the archwire connector 122 is a clip made of a resilient material that can deform in order to receive the archwire within the open interior 124 of the archwire connector 122 and then return to an original shape of the archwire connector 122 in order to retain the archwire within the archwire connector 122. The archwire connector 122 is secured to the rod 56 of the orthodontic appliance exemplarily by welding or brazing, although other types of connections may be used within the scope of the disclosure. In one feature of the exemplary embodiment, the archwire connector 122 depicted in FIG. 14 is that an opening 128 of the archwire connector 122 is directed downwardly such that the orthodontic appliance is connected to the archwire using the archwire connector 122 with a downward motion relative to the archwire, which in some embodiments may facilitate installation of the orthodontic appliance.

Embodiments of the archwire connector as disclosed herein provide advantages over previous solutions for the connection of orthodontic appliances in that the archwire connectors as disclosed herein facilitate the attachment and removal of the orthodontic appliance to and from the patient's already installed archwire, without complete or partial removal of the archwire, or the removal of existing brackets or buccal tubes and replacement with specialized brackets, buccal tubes, or bands for securing the orthodontic appliance.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:
1. An orthodontic appliance comprising:
   a telescopic assembly comprising at least an end tube with a hollow interior and a telescopic member telescopically disposed within the end tube;
   a distal connector secured to the end tube at a generally distal end of the telescopic assembly, the distal connector comprising an eyelet configured to engage a screw;

a mesial connector secured to a generally mesial end of the telescopic assembly;

a cover having a generally tubular shape, a key slot, a cut out, and at least one latch projecting from the cover and radially exterior of the cut out, the cover configured to removably engage and at least partially surround at least a portion of the end tube and the distal connector is slidably received in the key slot to position the distal connector to radially extend exterior of the cover through the cut out, the at least one latch releaseably engages the distal connector at a position below the eyelet to releasably secure the cover, an end cap, and a first spring to the telescopic assembly;

the end cap secured to a distal end of the cover and removably engages the distal end of the end tube; and the first spring secured at a distal end to the end cap and the spring extends away from the end cap coaxially within the end tube, the first spring configured to impart a first biasing force against the end cap and the telescopic member.

2. The orthodontic appliance of claim 1, further comprising a rod telescopically disposed within the telescopic member and the end tube, the rod forming the mesial end of the telescopic assembly.

3. The orthodontic appliance of claim 2, wherein the distal connector is secured to a distal end of the end tube and extends distally away from the distal end of the end tube.

4. The orthodontic appliance of claim 1,
wherein the end cap is secured to a distal end of the cover and the end cap removably engages the distal end of the end tube and the first spring is interchangeable with a second spring configured to impart a second biasing force against the end cap and the telescopic member.

5. The orthodontic appliance of claim 4, wherein the cover, end cap, and first spring are coupled together as a first interchangeable spring assembly.

6. The orthodontic appliance of claim 5, further comprising a second interchangeable spring assembly comprising the second spring, a second cover, and a second end cap, the first interchangeable spring assembly configured to impart the first biasing force against the distal end of the telescopic member, and the second interchangeable spring assembly configured to impart the second biasing force against the distal end of the telescopic member.

7. The orthodontic appliance of claim 6, wherein the end cap of each of the first and second interchangeable spring assemblies further comprises an indicia indicative of the alternative biasing force of the spring of each of the first and second interchangeable spring assemblies.

8. The orthodontic appliance of claim 4, wherein the first spring is configured to impart a first effective engagement range and the second spring is configured to impart a second effective engagement range.

9. The orthodontic appliance of claim 1, further comprising a projection extending from the cover, the projection facilitates the application of a force to disengage the at least one latch from the distal connector during removal of the cover, end cap, and spring.

10. The orthodontic appliance of claim 1, wherein the distal connector and the mesial connector are configured to couple to respective positions on a dentition of a patient and the cover is removable from engagement with the end tube while maintaining the coupling between the distal connector, the mesial connector and the dentition of the patient.

11. The orthodontic appliance of claim 1, wherein the distal connector comprises a first screw and the medial connector comprises a second screw, and further comprising a first archwire connector having a body with a threaded through-hole coupled to the first screw of the distal connector and a second archwire connector having a body with a threaded through-hole coupled to the second screw of the mesial connector, the archwire connectors each comprising a lip which defines a wire slot between the lip and the body of the connector, a respective archwire received within the wire slot and secured within the wire slot by the respective first screw and second screw that extends through the threaded through-hole to at least partially obstruct the wire slot.

12. The orthodontic appliance of claim 11 wherein the wire slot of the first archwire connector is defined between the body and lip of the first archwire connector and the first screw, the respective archwire moveably secured within the wire slot of the first archwire connector; and
wherein the wire slot of the second archwire connector is defined between the body and lip of the second archwire connector and the second screw, the respective archwire moveably secured within the wire slot of the second archwire connector.

13. The orthodontic appliance of claim 1 further comprising a first archwire connector coupled to the distal connector and a second archwire connector coupled to the mesial connector, wherein the distal connector and the mesial connector further comprise respective screws and the first and second archwire connectors comprise threaded holes and a pair of resilient arms defining an archwire bore, at least one archwire is received within the archwire bores to secure the orthodontic appliance to at least one archwire and the respective screws are threadedly received in the threaded holes to secure the archwire connectors to the distal connector and the mesial connector.

14. A method of treating a malocclusion with an orthodontic appliance, the method comprising:
securing an orthodontic appliance at mesial and distal ends of the orthodontic appliance to two locations within the dentition of the patient, the orthodontic appliance comprising:
a telescopic assembly comprising at least an end tube with a hollow interior and a telescopic member telescopically disposed within the end tube;
a distal connector secured to the end tube at a generally distal end of the telescopic assembly, the distal connector comprising an eyelet configured to engage a screw;
a mesial connector secured to a generally mesial end of the telescopic assembly; and
a first interchangeable spring assembly comprising a cover having a generally tubular shape, a key slot, a cut out, and at least one latch projecting from the cover and radially exterior of the cut out, the cover configured to removably engage and at least partially surround at least a portion of the end tube and the distal connector is slidably received in the key slot to position the distal connector to radially extend exterior of the cover through the cut out, the at least one latch releasably engages the distal connector at a position below the eyelet to releasably secure the cover, an end cap, and a spring to the telescopic assembly, the end cap secured to a distal end of the cover and removably engaged to the distal end of the end tube, and the spring secured at a distal end to the end cap and the spring extends away from the end cap coaxially within the cover and the end tube, the spring configured to impart a first biasing force against the end cap and the telescopic member;
selecting a second interchangeable spring assembly from a plurality of interchangeable spring assemblies, the second interchangeable spring assembly of the plurality configured to impart a second biasing force against the distal end of the telescopic member;

removing the first interchangeable spring assembly from engagement with the end tube;

engaging the second interchangeable spring assembly with the end tube; and progressing treatment by imparting the second biasing force against the end cap and the telescopic member.

15. The method of claim 14, further comprising maintaining securement between the orthodontic appliance and the two locations within the dentition of the patient while removing the first interchangeable spring assembly from engagement with the end tube and engaging the end tube with the second interchangeable spring assembly.

16. The method of claim 15, wherein the distal connector and the mesial connector of the orthodontic appliance further comprise respective cup-and-ball screws, the respective cup-and-ball screws secure the orthodontic appliance to the two locations within the dentition of the patient.

17. The method of claim 15, further comprising rotating the orthodontic appliance relative to the dentition of the patient about the respective cup-and-ball screws to facilitate the removing the first interchangeable spring assembly and engaging the second interchangeable spring assembly.

\* \* \* \* \*